(12) United States Patent
Burroughs et al.

(10) Patent No.: US 6,221,046 B1
(45) Date of Patent: *Apr. 24, 2001

(54) RECYCLABLE MEDICATION DISPENSING DEVICE

(75) Inventors: Andrew Burroughs, Kenosha, WI (US); Dave Hixson, Evanston, IL (US); Andrew Hodge, San Francisco, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/678,528

(22) Filed: Jul. 9, 1996

Related U.S. Application Data

(63) Continuation-in-part of application No. 08/399,764, filed on Mar. 7, 1995, now abandoned.

(51) Int. Cl.[7] .............................. A61M 1/00; A61M 5/00; A61M 5/315
(52) U.S. Cl. .................. 604/153; 604/207; 604/220; 604/232; 604/208
(58) Field of Search .................................... 604/207, 208, 604/209, 210, 211, 181, 186, 187, 232, 224, 218, 220, 228, 229, 71, 72, 404, 246; 222/309, 390, 391

(56) References Cited

U.S. PATENT DOCUMENTS

| | | |
|---|---|---|
| 4,413,760 | 11/1983 | Paton . |
| 4,592,745 | 6/1986 | Rex et al. . |
| 4,865,591 * | 9/1989 | Sams . |
| 4,883,472 | 11/1989 | Michel . |
| 4,936,833 * | 6/1990 | Sams . |
| 4,973,318 * | 11/1990 | Holm et al. . |
| 5,017,190 | 5/1991 | Simon et al. . |
| 5,042,977 * | 8/1991 | Bechtold . |
| 5,085,641 | 2/1992 | Sarnoff et al. . |
| 5,092,842 * | 3/1992 | Bechtold et al. ............... 604/209 |
| 5,104,380 | 4/1992 | Holman et al. . |
| 5,112,317 | 5/1992 | Michel . |
| 5,114,406 * | 5/1992 | Gabriel et al. . |
| 5,232,459 | 8/1993 | Hjertman . |
| 5,244,465 | 9/1993 | Michel . |
| 5,279,585 | 1/1994 | Balkwill . |
| 5,279,586 | 1/1994 | Balkwill . |
| 5,295,976 | 3/1994 | Harris . |
| 5,304,152 | 4/1994 | Sams . |
| 5,308,340 | 5/1994 | Harris . |

(List continued on next page.)

FOREIGN PATENT DOCUMENTS

| | | |
|---|---|---|
| 349 592 | 5/1988 | (EP) . |
| 498 737 | 8/1992 | (EP) . |
| WO 92/18179 | 10/1992 | (WO) . |
| WO 93/07922 | 4/1993 | (WO) . |
| WO 94/15120 | 7/1994 | (WO) . |

*Primary Examiner*—Richard K. Seidel
*Assistant Examiner*—Michael J Hayes
(74) *Attorney, Agent, or Firm*—Michael T. Bates

(57) ABSTRACT

A multi-use medication dispensing pen made of a plastic material that is recyclable after the contents of the medication cartridge have been exhausted. The pen is made of a minimal number of parts, which include a housing, a dial mechanism, a generally cylindrical button assembly located within the proximal end of the dial mechanism, an internally threaded nut, and an externally threaded leadscrew. The pen is arranged so that the dial mechanism must be rotated to the zero-dose position prior to setting a dose. The pen includes a lockout mechanism that prevents the dial mechanism from being inadvertently depressed during dosing. The pen further includes a mechanism that limits the maximum dosage that can be dialed up and a mechanism that prevents the user from dialing up a dosage greater than that remaining in the cartridge.

23 Claims, 4 Drawing Sheets

U.S. PATENT DOCUMENTS

| | | |
|---|---|---|
| 5,370,629 | 12/1994 | Michel et al. . |
| 5,383,865 * | 1/1995 | Michel . |
| 5,582,598 * | 12/1996 | Chanoch .............................. 604/208 |
| 5,591,136 * | 1/1997 | Gabriel ................................ 604/208 |
| 5,611,783 * | 3/1997 | Mikkelsen ............................ 604/211 |
| 5,626,566 * | 5/1997 | Petersen et al. ..................... 604/208 |
| 5,938,642 * | 8/1999 | Burroughs et al. .................. 604/208 |

* cited by examiner

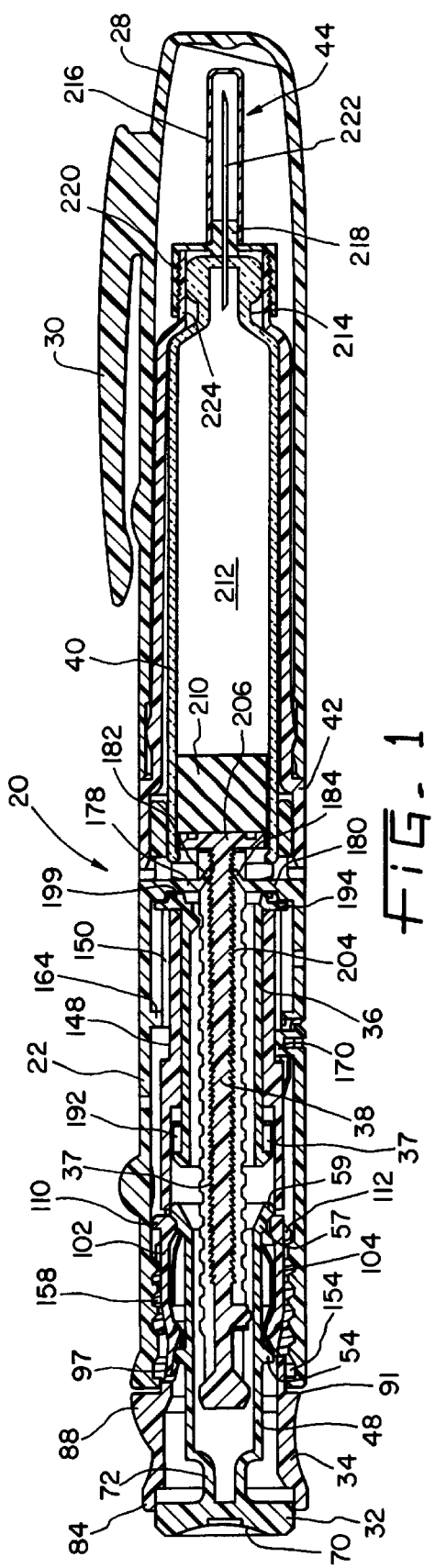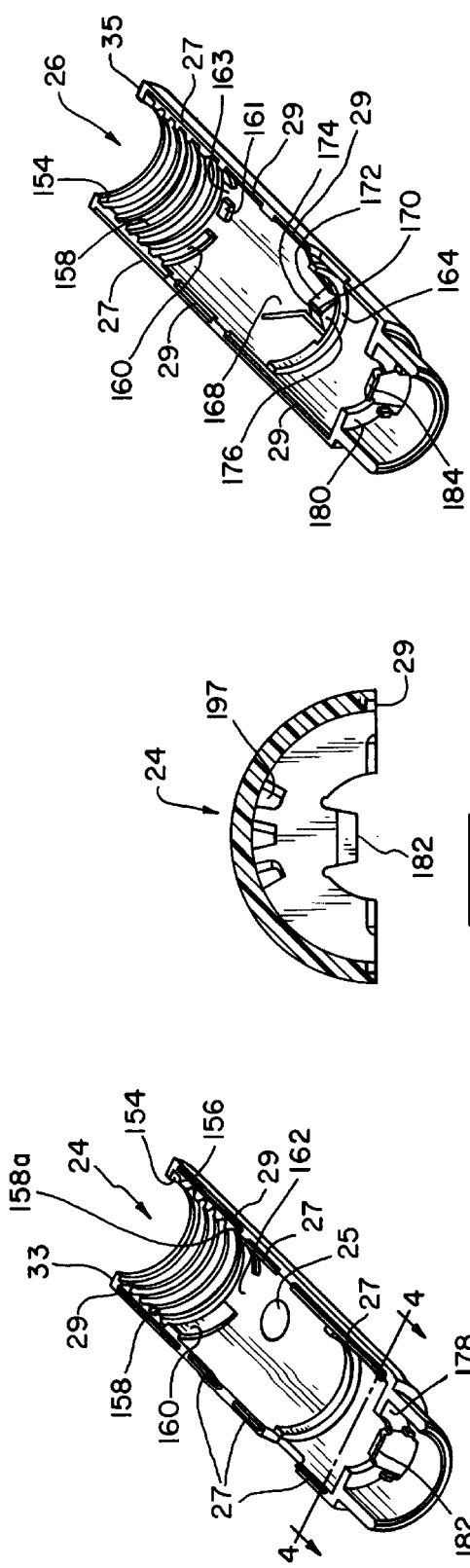

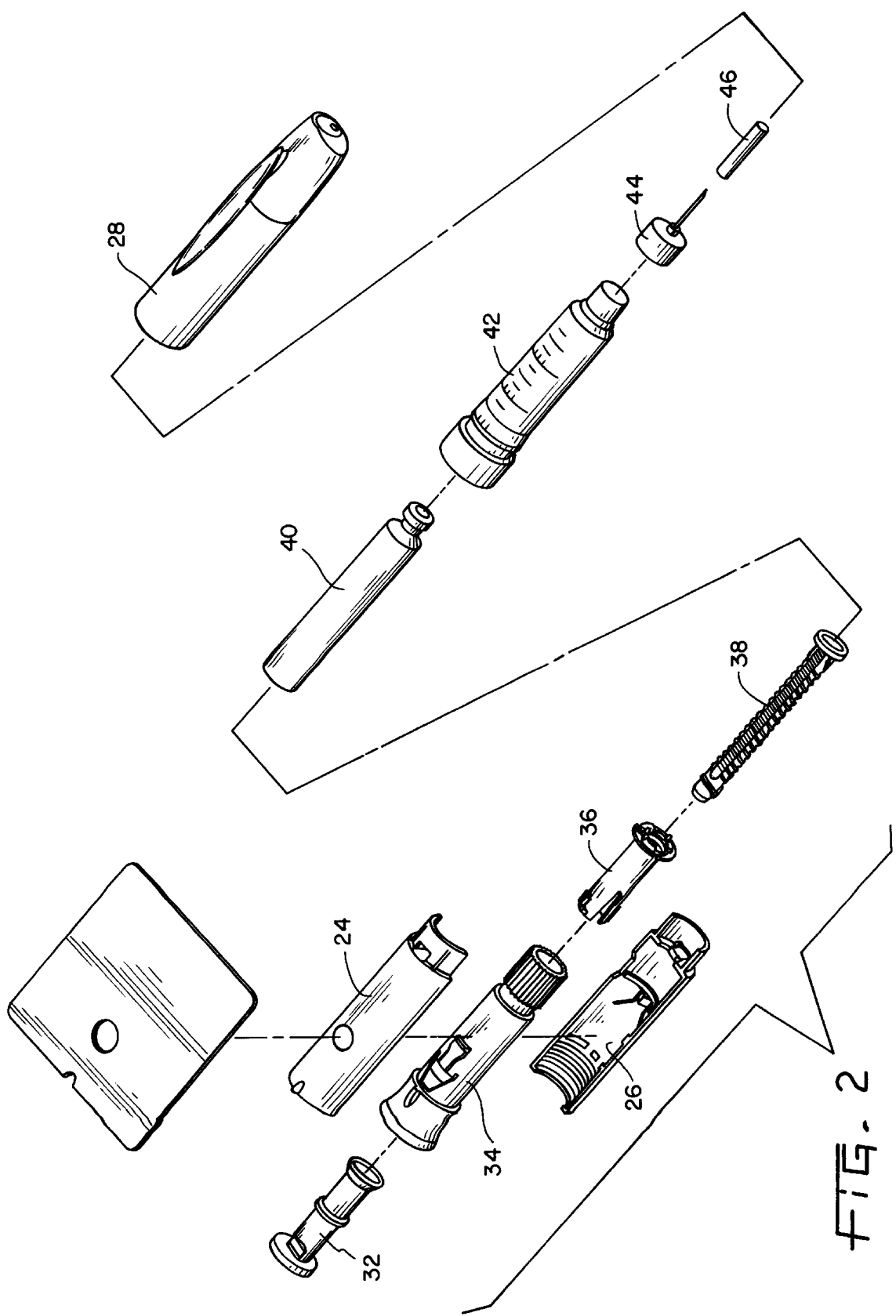

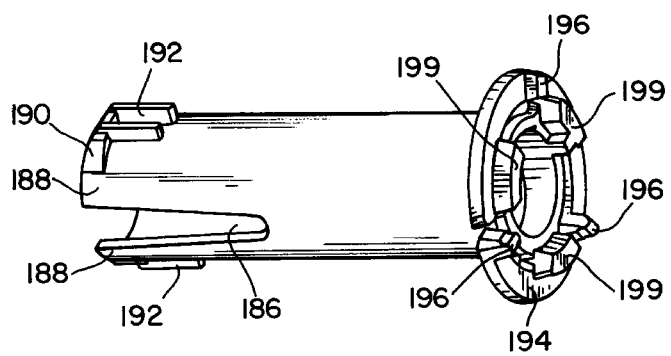
FIG. 10
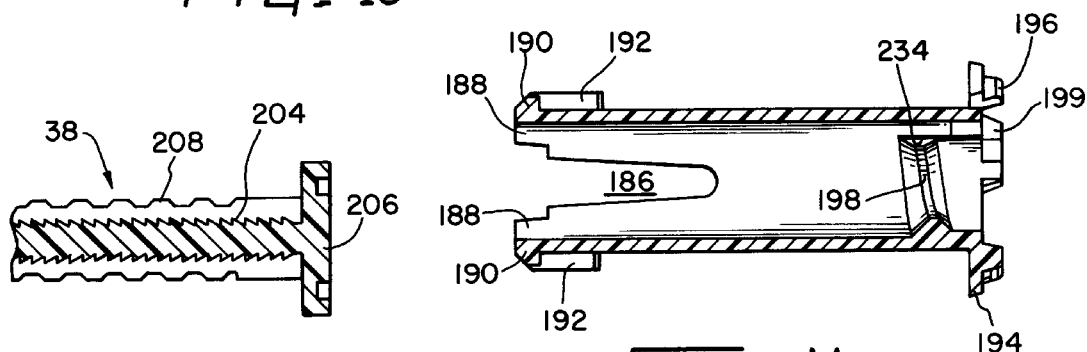
FIG. 13
FIG. 11
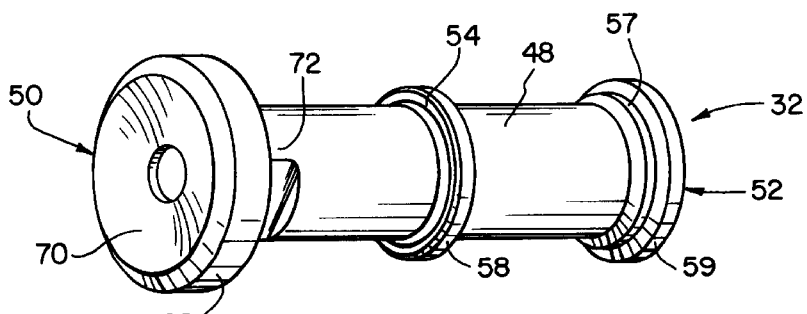
FIG. 14
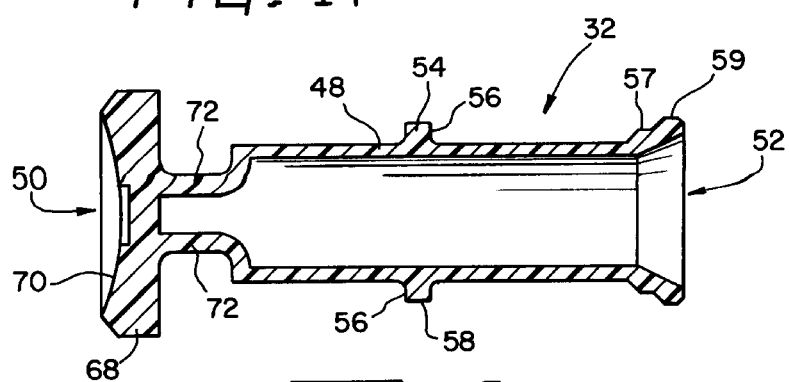
FIG. 15

RECYCLABLE MEDICATION DISPENSING DEVICE

CROSS REFERENCE TO RELATED APPLICATION

This is a of U.S. patent application Ser. No. 08/399,764, titled RECYCLABLE MEDICATION DISPENSING DEVICE, which was filed on Mar. 7, 1995, now abandoned.

BACKGROUND OF THE INVENTION

1. Field of the Invention

The present invention relates generally to medical dispensing devices and, more particularly, to recyclable dispensing devices that permit selectively measured dosages of a liquid to be dispensed.

2. Background of the Related Art

Patients suffering from diseases such as diabetes must inject themselves several times each day with an insulin solution. Since the volume of insulin solution to be injected varies from injection to injection, it is necessary for such patients to be able to measure a precise volume of insulin. Diabetics have conventionally used a syringe for injection of insulin. However, it is difficult to control the operation of the syringe as well as the quantity of drug injected.

In order to permit a diabetic to measure and administer a more accurate and controlled dosage, injector pens have been developed which enable a particular dosage to be accurately and conveniently measured. Generally, these pens are secured onto a cartridge having a particular quantity of liquid medication sealed therein. The cartridge includes a plunger and a mechanism for advancing the plunger in the cartridge in a manner to dispense the medication. Injector pens may be reusable or disposable. In reusable pens, a user can change a spent cartridge and reset the leadscrew of the pen back to its initial position. In a disposable pen, the cartridge is permanently captured in the pen which is disposed of after the contents of the cartridge have been exhausted.

One such disposable pen that has functioned very adequately is disclosed in U.S. Pat. No. 5,295,976. Specifically, a dispensing device is disclosed and includes an internally threaded collar and an externally threaded plunger rod. In order to set a dosage of medication to be delivered, the collar is rotated thereby causing displacement of the collar toward the proximal end of the injection device. Rotation of the collar causes the integral cap to become effectively displaced both rotationally and axially toward the proximal end of the pen. As this displacement occurs, the segment of the dose-indicating scale which is visible through a window varies to show a linear increase in the number to indicate an increased dosage of liquid to be dispensed. Once the desired dosage is selected, a force is applied to the end of the cap causing a linear displacement of the cap, integral plunger rod, and piston to dispense liquid from the container. The dispensing displacement of the plunger rod is halted by abutting contact between the cap and a stop element.

In U.S. Pat. No. 5,308,340, another recyclable injection device is disclosed. In particular, a plunger rod is received within the housing for exerting a force on a piston closing a second end of the container. The plunger rod has a noncylindrical cross section with a first surface including threads and a second surface which can, optionally, include a series of ratchet teeth. A collar is received within the housing adjacent the second end of the container for permanently retaining the container of liquid within the housing. The plunger rod passes through the noncylindrical opening in the collar and is prevented from rotating with respect to the housing by the collar. A hollow cap envelopes the plunger rod opposite the container of liquid. The skirt of the hollow cap extends inside the housing. The cap includes a threaded interior surface which movably engages the plunger rod for calibrated adjustment relative thereto. A stop is provided within the housing, and a distal facing surface is provided on the hollow cap for contacting the stop upon linear movement of the cap and plunger rod as a unit toward the container to dispense liquid therefrom. In operation, the cap is rotated in a counterclockwise direction causing the threads of the cap to travel along the threaded portion of the rod. This rotation does not cause displacement of the plunger rod with respect to the housing, but backs the distal end of the proximal cap portion away from a stop shoulder on the inside of the housing. When the cap has been positioned to the desired dosage, pressure is applied to the end of the cap for causing it to move linearly toward the distal end of the housing until a shoulder defined by a radially exposed portion of the distal end contacts a stop.

Finally, in U.S. patent application Ser. No. 08/399,764, the parent application to the present application, a medication dispensing device is disclosed which includes a dial telescopingly disposed within a housing wherein the dial can be engaged with a nut disposed on a lead screw. The lead screw, in conjunction with the dial and the nut, ultimately serves as a plunger to eject the medication from a cartridge contained within the device. If the dial is rotated while not engaging the nut, a dosage will not be set, and in order to commence an injection, a button assembly must be depressed relative to the dial to disengage the dial from the housing. The disclosure of U.S. patent application Ser. No. 08/399,764 is incorporated by reference herein.

SUMMARY OF THE INVENTION

The present invention provides a medication injection device comprising a housing, a dose setting mechanism within the housing, and a delivery mechanism within the housing for advancing a leadscrew. A liquid medication product is housed in a variable volume cartridge within the housing of the device. Upon actuation of the delivery mechanism, the leadscrew is advanced against a movable piston in the cartridge to advance the piston, thereby causing a preset quantity of medication to be delivered from the needle of the device.

In one embodiment, the device is made entirely out of a recyclable plastic material, except for the glass container, steel needle and paper label. The dose setting mechanism comprises a dial mechanism including a clutching device for engaging and disengaging a generally cylindrical internally threaded nut, which is threaded onto an externally threaded leadscrew. A dose is set by rotating the nut with respect to the leadscrew. The nut is rotated by rotating the dial mechanism. However, the nut must be engaged with the dial mechanism so that rotating the dial mechanism also rotates the nut. The clutching device comprises a series of splines on the inner cylindrical surface of the dial mechanism which axially engage corresponding splines on the outer surface of the nut. The splines are engaged with one another by retracting the dial mechanism with respect to the nut after the dial mechanism has been rotated to its zero-dose position.

The dial mechanism includes a mechanism that prevents the user from retracting the dial mechanism prior to rotating the dial mechanism to its zero-dose position. The dial mechanism cannot be pulled out in any radial position other than the zero-dose radial position due to the interference formed between threads formed on elastically deformable tabs extending from the dial mechanism and a raised surface formed on the inner circumference of the housing. The threads are specifically shaped and arranged such that they align with openings in the raised surface in only one position, the zero-dose position, in the 360° circumference of the housing.

The device includes a mechanism that limits the maximum dosage that can be set. This mechanism comprises a helical groove formed in the housing and a pair of flexible tabs, having threads integral therewith, formed in the dial mechanism. Upon rotating the dial mechanism to set a dose, the dial mechanism is retracted with respect to the housing and the threads on the dial tabs ride up the internal housing groove. Once the dial threads reach the proximal end of the housing groove, further rotation of the dial mechanism is prohibited, thereby indicating to the user that the maximum dosage has been dialed.

The device further includes a mechanism for automatically locking out the dial mechanism from an inadvertent injection after the dial mechanism has been retracted to set a dosage. This lockout mechanism comprises the above-mentioned threads in the dial mechanism that ride up the helical groove in the housing upon retracting the dial mechanism with respect to the housing. The interference fit formed by the threads in the groove prevents forward movement of the dial mechanism in the event of inadvertent pressure being applied to the end of the dial mechanism. The lockout mechanism is released by a button that is disposed within the proximal end of the dial mechanism. The button is sized and configured so that it must be depressed upon initiating an injection. Upon depressing the button, the button moves forward so that the flexible tabs and associated threads move inward and out of engagement with the groove to allow the dial mechanism to move relative to the housing.

The device also includes an "end-of-injection click" feature which includes an extension on one of the two flexible tabs of the dial mechanism which, when the button is pressed, is pushed radially out. This finger falls within a separate groove in the housing as the end-of-injection stop surface of the nut engages the corresponding stop surface on the housing, thereby producing an audible "click" indicating that the entire dosage has been injected.

The housing further includes radially inwardly extending tangs at the distal end of the housing which engage ratchet teeth in the leadscrew to prevent the leadscrew from backing up in the proximal direction. These tangs are in constant engagement with the leadscrew, thereby preventing the leadscrew from rotating upon rotation of the nut.

The device also includes a mechanism which indicates to the user that there is an insufficient dosage remaining in the cartridge of medication. This mechanism prevents the user from setting a dosage greater than that available to be delivered. The insufficient dose remaining feature comprises an approximately 350° helical thread on the inner cylindrical surface of the nut and a raised key at the end of the leadscrew where the external thread terminates. As the nut rotates about the leadscrew, the ledge formed by the termination of the helical thread on the nut engages the key, thereby positively preventing further rotation of the nut in that direction and indicating the device contains an insufficient remaining dose.

The present device also includes a mechanism which prevents rotation of the nut when the dial mechanism is in its end-of-injection position. If the nut were allowed to rotate while the dial mechanism was in the end-of-injection position, the nut would in turn move along the leadscrew and potentially result in an inaccurate dosage. The present device therefore provides a plurality of prongs around the circumference of the distal nut flange and a corresponding plurality of ribs on the inner circumference of the housing distal end. In the end-of-injection position, the prongs engage the ribs to allow the dial mechanism to rotate while maintaining the rotational position of the nut, and when the dial mechanism is in the dose-setting position, the dial mechanism is retracted and the nut prongs are permitted to flex away from the ribs to allow for the nut to rotate about and axially move along the leadscrew.

An advantage of the medication dispensing device of the present invention is that the dosing function is locked out until the dial mechanism has been rotated to its zero-dose position, thereby enabling the dial mechanism to be retracted to the dose-setting position and ensuring an accurate dosage.

Another advantage of the present invention is that the device is an inexpensive recyclable pen that is designed to allow a user to dose in single unit increments, which are each displayed in a single unit display.

Another advantage of the present invention is that the end-of-injection click indicator is coordinated with the end-of-injection stop to provide increased accuracy in determining the end of a injection.

Another advantage of the present invention is that the device includes a dosage lockout mechanism that prevents an inadvertent delivery of a dosage of medication.

A further advantage of the present invention is that the insufficient remaining dose mechanism comprises a radial stop which ensures that the user cannot dial up a dosage greater than that remaining in the cartridge.

Yet another advantage of the present invention is that the device is made of inexpensive materials and is nearly 100% recyclable after the contents of the cartridge have been depleted.

Yet another advantage of the present invention is that the device includes a mechanism to prevent rotation of the nut while the dial mechanism is in the end-of-injection position.

The present invention, in one form thereof, provides a medication injection pen having a distal end and a proximal end. The pen comprises a housing, a cartridge, a drive stem, a rotatable nut, and a dial mechanism. The cartridge is mounted within the housing and includes a piston, an exit, and injectable medication between the piston and the exit. The drive stem is disposed within the housing in axial alignment with the cartridge and is adapted to axially move through the cartridge for driving the piston and ejecting medication from the cartridge. The rotatable nut is disposed within the housing and is threadably engaged with the drive stem. The dial mechanism is rotatable, axially shiftable, and includes an end-of-injection axial position and a dose-setting axial position. The dial mechanism is rotatably engaged with the nut when in the dose-setting position whereby rotation of the dial mechanism relative to the housing causes the nut to rotate relative to the drive stem to thereby set a dose. The dial mechanism is axially engaged with the nut during injection to thereby drive the drive stem forward. The housing includes at least one rotation preventing lock element which is engageable by a mating lock element on the nut when the dial mechanism is in the end-of-injection axial position to thereby prevent the nut from rotating.

The present invention, in one form thereof, provides a medication injection pen having a distal end and a proximal end. The pen comprises a housing, a cartridge, a drive stem, a rotatable nut, and a dial mechanism. The cartridge is mounted within the housing and includes a piston, an exit, and injectable medication between the piston and the exit. The drive stem is disposed within the housing in axial alignment with the cartridge and is adapted to axially move through the cartridge for driving the piston and ejecting medication from the cartridge. The rotatable nut is disposed within the housing and is threadably engaged with the drive stem. The dial mechanism is rotatable, axially shiftable, and includes an end-of-injection axial position and a dose-setting axial position. The dial mechanism is rotatably engaged with the nut when in the dose-setting position whereby rotation of the dial mechanism relative to the housing causes the nut to rotate relative to the drive stem to thereby set a dose. The dial mechanism is axially engaged with the nut during injection to thereby drive the drive stem forward. A damping compound is disposed between the dial mechanism and the nut to provide relatively slow, smooth, and quiet movement from the dose- setting position to the end-of-injection position.

The present invention, in yet another form thereof, provides a medication injection pen having a distal end and a proximal end. The pen comprises a housing, a cartridge, a drive stem, a rotatable nut, and a dial mechanism. The housing includes a circular groove about an inner circumference thereof. The cartridge is mounted within the housing and includes a piston, an exit, and injectable medication between the piston and the exit. The drive stem is disposed within the housing in axial alignment with the cartridge and is adapted to axially move through the cartridge for driving the piston and ejecting medication from the cartridge. The rotatable nut is disposed within the housing and is threadably engaged with the drive stem. The dial mechanism is rotatable, axially shiftable, and includes an end-of-injection axial position and a dose-setting axial position. The dial mechanism is rotatably engaged with the nut when in the dose-setting position whereby rotation of the dial mechanism relative to the housing causes the nut to rotate relative to the drive stem to thereby set a dose. The dial mechanism is axially engaged with the nut during injection to thereby drive the drive stem forward. The dial mechanism includes an end-of-injection click finger which is elastically deformable relative to the dial mechanism, and which snaps into the housing circular groove when an injection is complete to provide the user with an audible indication thereof.

The present invention, in another form thereof, provides a medication injection pen having a distal end and a proximal end. The pen comprises a housing, a cartridge, a drive stem, a rotatable nut, and a dial mechanism. The housing includes a helical groove disposed on an inner circumference thereof about its proximal end. The cartridge is mounted within the housing and includes a piston, an exit, and injectable medication between the piston and the exit. The drive stem is disposed within the housing in axial alignment with the cartridge and is adapted to axially move through the cartridge for driving the piston and ejecting medication from the cartridge. The rotatable nut is disposed within the housing and is threadably engaged with the drive stem. The dial mechanism is rotatable, axially shiftable, and includes an end-of-injection axial position and a dose-setting axial position. The dial mechanism is rotatably engaged with the nut when in the dose-setting position whereby rotation of the dial mechanism relative to the housing causes the nut to rotate relative to the drive stem to thereby set a dose. The dial mechanism is axially engaged with the nut during injection to thereby drive the drive stem forward. The dial mechanism further includes first and second threads on an inner circumference thereof which are adapted to ride along the housing helical groove and elastically deform inward and outward relative to the dial. The button is telescopingly received in the proximal end of the dial mechanism, and includes a distal end having a first circumferential step and a second circumferential step. The first step has an enlarged diameter, and the second step has a larger diameter than the first step. The first step engages and biases the elastically deformable threads outward such that the threads engage the helical groove and prevent the dial mechanism from being telescopingly inserted into the housing. The second step engages the dial mechanism to prevent the button from being fully retracted out of the pen. The button is adapted to telescopingly insert into the dial to thereby move the button first step out of engagement with the deformable threads to thereby allow the threads to deform inward and out of engagement with the helical groove. The dial mechanism is thereby able to telescopingly insert into the housing to drive the nut, drive stem, and piston for injection of the medication.

The present invention, in still another form thereof, provides a method of manufacturing a medication injection pen housing comprising the steps of disposing first and second semi-cylindrical plastic portions having longitudinal edges around a dosage setting and injection apparatus such that the portions form a cylindrical housing, and ultrasonically welding the portions together wherein the portions are vibrated at a frequency sufficient to melt the longitudinal edges. The portions are secured together when the plastic hardens.

BRIEF DESCRIPTION OF THE DRAWINGS

The above mentioned and other features and objects of this invention, and the manner of attaining them, will become more apparent and the invention itself will be better understood by reference to the following description of the invention taken in conjunction with the accompanying drawings wherein:

FIG. 1 is a sectional assembly view of the present invention;

FIG. 2 is an exploded view of the embodiment shown in FIG. 1;

FIG. 3 is a perspective view of the housing first part which forms one-half of the housing of the present invention;

FIG. 4 is a sectional view of the element shown in FIG. 3 taken along line 4—4;

FIG. 5 is a perspective view of the housing second part which forms the other half of the housing of the present invention;

FIG. 10 is a perspective view of the nut;

FIG. 11 is a sectional view of the embodiment shown in FIG. 10;

FIG. 13 is a sectional cutaway view of the embodiment shown in FIG. 12;

FIG. 14 is a perspective view of the button; and

FIG. 15 is a sectional view of the button.

Corresponding reference characters indicate corresponding parts throughout the several views. The exemplification set out herein illustrates an exemplary embodiment of the invention and such exemplification is not to be construed as limiting the scope of the invention in any manner.

DESCRIPTION OF THE PREFERRED EMBODIMENT

Figure 6:
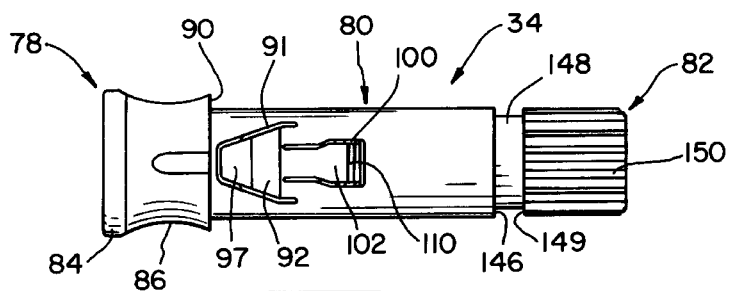
FIG. 6 is a plan view of the dial.

For purposes of this application, the term "proximal"shall designate a relative axial position toward the button end of the delivery pen, and the term "distal" shall designate a relative axial position toward the delivery needle end of the delivery pen.

Referring to FIGS. 1 and 2, there is shown an injection medication device 20 having the general appearance of a pen or mechanical pencil. The device comprises a mechanism housing 22 having a first part 24 and a second part 26 (FIG. 2). Housing parts 24 and 26 are secured together by ultrasonic welding wherein, as shown in FIG. 3 and FIG. 5, rectangular projections 27 extending from housing parts 24 and 26 are inserted into V-shaped grooves 29 also provided in housing parts 24 and 26 and the two housing parts 24 and 26 are then vibrated at a frequency sufficient to melt projections 27 where projections 27 contact V-shaped grooves 29. The melted plastic then hardens and housing parts 24 and 26 are thereby secured together. A cap 28 is snapped onto the distal end of mechanism housing 22. As best shown in FIG. 1, cap 28 includes a clip 30 which cooperates with the side wall of cap 28 to provide a convenient means for holding the pen device 20 in a shirt pocket.

Referring to FIG. 2, the other major components of medication device 20 include button 32, dial mechanism 34, nut 36, and a drive stem in the form of leadscrew 38. Cartridge 40 is inserted into distal body 42 to which is attached needle assembly 44 and needle cover 46. All of the components of medication device 20, except cartridge 40 and needle 44 may be made of a plastic material that is suitable for recycling. Suitable plastics are polycarbonate resins which can be processed by conventional injection molding and extrusion. In one embodiment, the housing parts 24, 26 and distal body 42 are made from an optically clear polycarbonate material, and the remaining plastic components are made from ABS resins. These plastics are recyclable, thereby making disposal of the device environmentally desirable.

Referring to FIG. 14 and FIG. 15, button 32 comprises a hollow cylindrical portion 48 having a proximal end 50. Cylindrical portion 48 includes a distal end 52 in the form of a double-stepped annular bead and further includes an enlarged diameter ring 54 comprising a ledge surface 56 and an enlarged diameter flat surface 58. The double-stepped distal end 52 includes a first step 57 and a second step 59. As shown in FIG. 1, first step 57 is used to prevent dial tabs 102 and 104 from collapsing inward, and second step 59 is used both to keep button 32 centered within dial mechanism 34 and also prevent button 32 from inadvertently falling or being removed from dial 34. Proximal end 50 of button 32 further includes a finger-engageable end 68 having a recessed surface 70. End 68 is integrally connected to hollow cylindrical portion 48 by connection portion 72 (FIG. 15). In the exemplary embodiment, end 68 protrudes 1.5 millimeters beyond the end of dial mechanism 34 to enable the user to easily depress the button during injection.

Figure 7:
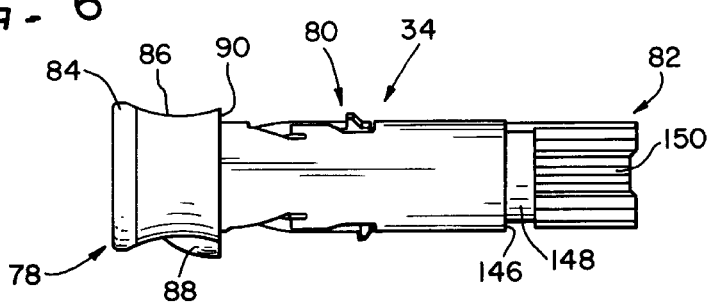
FIG. 7 is a plan view of the embodiment shown in FIG. 6 rotated 90°.

Referring to FIGS. 6–9, dial mechanism 34 is shown in detail. Dial mechanism 34 is generally cylindrical in shape and is hollow throughout its axial length. The diameter of dial mechanism 34 is at a maximum at its proximal end and is at a minimum at its distal end. Dial mechanism 34 comprises proximal portion 78, intermediate portion 80, and distal portion 82. Proximal portion 78 comprises enlarged diameter portion 84, tapered portion 86, and ring 90 extending about the circumference of proximal portion 78. Ring 90 also includes an enlarged "zero-dose" protrusion 88 as best shown in FIG. 7.

Generally U-shaped grooves 91 and 93 (FIGS. 6, 8) are formed in intermediate portion 80 to form a flexible sections 92 and 95, respectively. As best shown in FIG. 9, the proximal ends of flexible sections 92 and 95 each include fingers 94 having ramped inner surfaces 96 adapted for engagement with enlarged diameter portion 54 of button 32. When button 32 is depressed, enlarged diameter portion 54 is also depressed and thereby pushes against ramped surfaces 96, which in turn forces fingers 94 outward and legs 102 and 104 inward. Dial mechanism 34 is then able to travel axially towards cartridge 40 during injection of the medical product as further discussed herein. shown in FIG. 6, flexible section 92 further includes a click finger 97 extending toward the proximal end of dial mechanism 34 which will also be described further herein.

Proximal portion 78 of dial mechanism 34 further includes a first U-shaped groove 100 (FIG. 6) and a second U-shaped groove 101 (FIG. 8) which form flexible legs 102, 104. Referring to FIG. 9, each leg 102, 104, respectively includes an inwardly extending finger 106, 108, and an outwardly extending thread 110, 112. Inwardly extending finger 106 includes proximal tapered surface 114, flat surface 116, and distal tapered surface 118. Likewise, finger 108 includes proximal tapered surface 120, flat surface 122, and distal tapered surface 124. Outwardly extending thread 110 comprises proximal shoulder 130, enlarged diameter surface 132, and distal tapered surface 134. Outwardly extending thread 112 includes shoulder 138, enlarged diameter surface 140, and distal tapered surface 142. Leg 102 and outwardly extending thread 110 are of lesser width than leg 104 and outwardly extending thread 112, and outwardly extending thread 112 is provided with a center keyway 133 as best shown in FIG. 8.

Referring to FIG. 9, there are shown a plurality of splines 144 extending circumferentially about the interior surface of intermediate portion 80 of dial mechanism 34. Splines 144 extend 360° about the inner circumference of intermediate portion 80 and engage with teeth 192 (FIGS. 10, 11) provided on nut 36 when the clutch is engaged to set a dosage. In one embodiment, eighteen splines 144 are positioned such each spline is 20 circumferential degrees apart from an adjacent spline.

Figure 8:
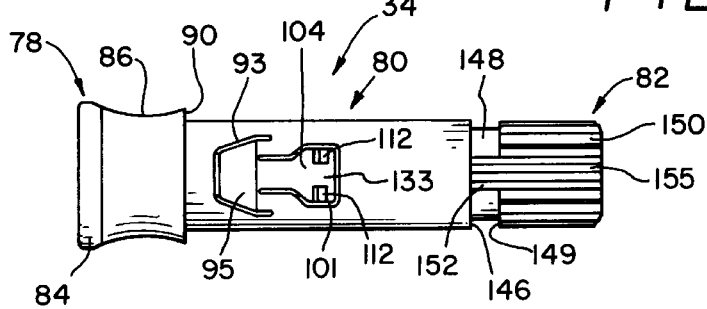
FIG. 8 is a plan view of the embodiment shown in FIG. 6 rotated 180°.
Figure 9:
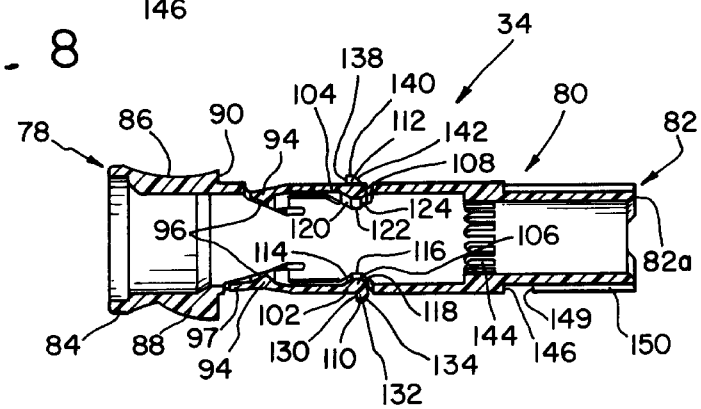
FIG. 9 is a sectional view of the embodiment shown in FIG. 7.

As best shown in FIGS. 6–8, distal portion 82 of dial mechanism 34 comprises a shoulder 146, a reduced diameter portion 148, and a distal end comprising a series of elongated splines 150 extending externally about the circumference of distal portion 82. Splines 150 are in rotational alignment with splines 144. Therefore, in one embodiment, there are eighteen splines 150, each corresponding to a respective spline 144. As shown in FIG. 8, two of the splines 150 extend axially into reduced diameter portion 148. These extensions are indicated as splines 152.

Referring to FIGS. 3 and 5, housing parts 24 and 26 form a proximal groove 154 having a tapered surface 156. Housing parts 24 and 26 further form a helical spiral groove 158 and a circumferential surface 160. Circumferential surface 160 includes opening 162 and keyed opening 163 to allow threads 110 and 112 respectively to enter helical groove 158 during the commencement of the dosing process. Housing parts 24 and 26 further include a circular centering ring 164 which circumscribes splines 150 to maintain proper alignment of dial 34. Housing part 26 includes grooves formed therein to define a flexible leg 168 having an inwardly extending finger 170 at the end thereof (FIG. 5). Finger 170 includes tapered surfaces 172, proximal end 174, and a distal end 176. Housing parts 24 and 26 include bulkhead ledges 178, 180, respectively, to reduce the diameter through the proximal end of the housing. Ledges 178 and 180 include flexible tangs 182, 184, respectively.

As best shown in FIGS. 1 and 2, medical delivery device 20 further includes nut 36 and leadscrew 38. Nut 36 is generally cylindrical in shape and includes a pair of axially extending grooves 186 (FIG. 10 and FIG. 11) to form resilient proximal legs 188. Each leg 188 includes a proximal raised portion 190 and two small axially extending splines 192. The distal end of nut 36 comprises a flange 194 having, in the exemplary embodiment, three teeth 196 thereon. Flange 194 also includes a raised surfaces 199 which contacts bulkhead ledges 178 and 180 to indicate to the user that the end of an injection has been reached. The interior surface of the distal end of nut 36 includes a helical thread 198. Thread 198 extends 350° about the inner surface of nut 36.

Figure 12:
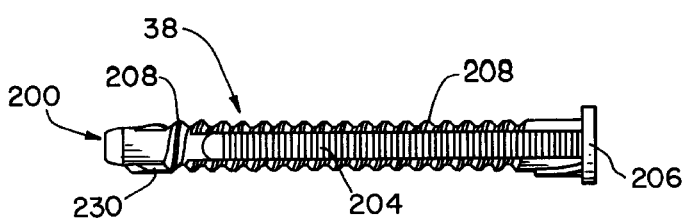
FIG. 12 is a plan view of the screw.

Referring now to FIGS. 12 and 13, leadscrew 38 is shown having a ratchet teeth 204 located on two opposing sides of leadscrew 38 and axially extending along the length of leadscrew 38 from proximal end 200 to plunger engagement portion 206. Helical threads 208 extend along the axial length of leadscrew 36. Leadscrew 38 fits within the cylindrical opening of nut 36. As shown in FIG. 1, plunger engagement portion 206 of leadscrew 38 is in engagement with piston 210 of cartridge 40. Cartridge 40 is housed within cartridge retainer 42, which is permanently secured to housing parts 24 and 26. Cartridge 40 is manufactured of glass and comprises a tube defining an inner chamber 212 which openly terminates at its distal end in a neck 214 having a cap 216 including a rubber disc 218 disposed thereover. Needle assembly 44 comprises an internally threaded base 220 and a delivery needle 222. Internally threaded base 220 is threaded onto externally threaded distal portion 224 of body 42. Needle cap 46 fits over needle 222 to prevent an inadvertent insertion of needle 222 into the patient. Cap 28 snaps onto cartridge body 42 to complete the pen-like mechanism.

In order to set a dose for injection, it is first necessary to manually zero dial mechanism 34 from the initial radial position of the dial resulting from the previous injection. In the initial radial position of dial mechanism 34 with respect to housing part 26, finger 170 of housing part 26 is located in groove 148 of dial mechanism 34. Groove 148 can be rotated by rotating dial mechanism 34 with respect to the housing. Dial mechanism 34 cannot be axially retracted due to the interference between threads 110 and 112 against surface 160. Likewise, dial mechanism 34 cannot be forced axially forward due to the interference between raised surface 199 of nut flange 194 and housing bulkhead ledges 178, 180. Upon continued rotation of dial 34 with respect to housing 26, splines 152 are moved into engagement with finger 170. This is the zero-dose radial position of dial 34. This zero-dose position is communicated to a user in four ways. The user hears a click as splines 152 engage finger 170. The movement of finger 170 over first spline 152 and into V-shaped recess 155 between splines 152 causes a vibration in device 20 that can be felt by the user. In addition, protrusion 88 on dial mechanism 34 is in axial alignment with protrusion 153 of housing part 24 (FIG. 1), thereby providing a visual indication that the zero-dose position has been reached. This is further visually communicated by the presence of a symbol in lens 25.

A series of numerals (not shown) are printed on the surface of intermediate portion 80 of dial mechanism 34. These numerals are helically spaced about the circumference of intermediate portion 80 and may number from 1 to 60, in single increments, to indicate a desired dosage. The lens 25 (FIG. 1) in housing part 24 is aligned with the numbers so that the appropriate number appears in the lens upon dialing up the dosage. A raised rectangular portion of lens 25 is located at the base of lens 25 to enhance the numerals thus making them easier to read.

In its zero-dose position, dial mechanism 34 may be axially retracted a predetermined distance, e.g. 3 to 5 mm, to engage the clutch mechanism. This places dial mechanism 34 into the dose-setting position. As dial mechanism 34 is retracted, ledge 149 is moved past housing finger 170 resulting in housing finger 170 being in engagement with splines 150. In addition, splines 144 of dial mechanism 34 are moved into engagement with splines 192 of nut 36 so that the adjacent lateral surfaces on the splines 144 and 196 will engage each other (FIGS. 4 and 11). When the surfaces are engaged, rotation of dial mechanism 34 causes corresponding rotation of nut 36. Rotation of leadscrew 38 is prevented by a key-keyway type of engagement between the anti-backup tangs 182 and 184 and leadscrew 38. As shown in FIG. 1, tangs 182, 184 form a key, and leadscrew 38 forms a keyway which comes into contact with the sides of the key. the zero-dose position, keyway 133 of leg 104 is aligned with key 161 in keyed opening 163 to allow threads 110 and 112, to enter helical groove 158, defined by helical land 158a, as shown in FIGS. 3 and 8. Upon rotation of dial 34, threads 110, 112 move within housing groove 158 in the proximal direction as dial mechanism 34 retracts from housing 22, thereby increasing the axial distance between ring 91 and surfaces 33, 35 of housing parts 24, 26. Rotation of dial mechanism 34 causes rotation of nut 36 so that internal helical raised groove 198 of nut 36 rotates along external threads 208 of leadscrew 38 to cause nut 36 to axially retract a corresponding axial distance. Rotation of dial mechanism 34 causes splines 150 to move past housing finger 170. The rotation of each spline 150 past finger 170 constitutes a single unit of dosage. As each spline 150 moves past finger 170, it causes a "click" to occur, thereby providing an audible indication of each unit of dosage dialed up. In addition, a single numeral appears in lens 25 after each unit rotation indicating the current dose selected. Once a dosage has been selected, that dosage may be made larger or smaller by rotating the dial assembly in either the clockwise or counterclockwise direction.

In one embodiment, dial mechanism 34 includes eighteen splines 150 spaced 20° apart from one another. It is desired to limit the amount of dosage that can be dialed to prevent the entire contents of cartridge 40 to be delivered at once. For example, it may be desirable to limit a measured dosage to a maximum of 60 units. If the dial assembly includes eighteen splines, this would mean that a user could rotate the dial assembly for nearly 3½ rotations. As a dosage is being set, outwardly extending threads 110 and 112 of dial mechanism 34 ride in helical groove 158 of housing parts 24 and 26. Once a predetermined maximum dosage has been dialed up, e.g. 60 units, threads 110 and 112 have reached the proximal end of the helical groove 158. Dial mechanism 34 cannot be additionally rotated to further increase this maximum dosage due to an interference ledge at the end of helical groove 158. Button 32 prevents dial 34 from being inadvertently pushed forward during the dosing process due to button surface 57 which forces threads 110, 112 of dial 34 into helical spiral groove 158 in housing parts 24, 26. Threads 110, 112 must be moved out of groove 158 before dial mechanism 34 may be moved axially forward. Threads 110, 112 can be moved out of engagement with groove 158 only after fully depressing button 32, thereby forcing enlarged diameter portion 54 into contact with ramped surfaces 96 and thereby moving distal button surface 57 out of engagement with legs 102 and 104 and thus removing threads 110, 112 from groove 158.

Once a desired dosage has been set, cap 28 is removed and needle cover 46 is removed to expose needle 222. The needle is inserted into the patient, and recessed surface 70 of button 32 is pushed. As button surface 70 is pushed into dial mechanism 34, button distal end 52 moves out of engagement with legs 102 and 104. Dial mechanism 34 is thereby able to move forward because threads 110, 112 are not in engagement with groove 158. As button 32 continues to be pressed, threads 110, 112 move past the remaining threads 158 in a like manner until dial mechanism 34 reaches its end-of-injection position shown in FIG. 1. The movement of click finger 97 into groove 154 creates an audible "click" sound, thereby providing an audible confirmation that the entire dosage has been injected.

As dial mechanism 34 is initially moved forward, splines 144 move out of engagement with splines 192 of nut 36 to disengage the clutch by rotationally decoupling dial mechanism 34 from nut 36 prior to any axial movement of nut 36. Dial mechanism 34 moves axially with respect to nut 36 until the distal end surface 82a of dial mechanism 34 engages nut flange 194 and moves nut 36 and leadscrew 38 forward to deliver the set dosage of medication.

Referring to FIG. 1, in order to provide for smooth, slow and quiet movement of dial mechanism 34 against nut 36, a damping compound 37 is provided therebetween. Damping compounds are commonly available on the market and in the exemplary embodiment, a damping compound manufactured by Nye Laboratories of Bancroft, Mass., is utilized. To also ensure a slow, smooth and quiet movement of leadscrew 38 through tangs 182, 184, damping compound 37 is disposed therebetween as well.

The end-of-injection stop feature limits axial movement of dial mechanism 34 and nut 36 relative to housing 22 by having raised surface 199 of nut flange 194 engage bulkhead ledges 178 and 180 of housing 22. In another embodiment, the end-of-injection stop may be designed to occur between ring 90 and proximal end surfaces 33, 35 of housing parts 24, 26, respectively.

Movement of leadscrew 38 is prevented in the proximal direction due to anti-backup tangs 182, 184 being in engagement with ratchet teeth 204. This assures that head 206 of leadscrew 38 remains in constant engagement with piston 210 at all times.

Once a dosage has been completed, the user releases his or her finger from recessed button surface 70. Upon releasing pressure from surface 70, the elastic bias resulting from ramped surfaces 96 forces button 32 back towards the proximal end of device 20 and to the automatic lock out position wherein threads 110 and 112 engage groove 158 to prevent dial mechanism 34 from being inadvertently advanced when dial mechanism 34 is again moved to a retracted position.

Medication device 20 further includes a mechanism to indicate to the user that there is an insufficient dosage of medication remaining in cartridge 40. Referring to FIG. 12, leadscrew 38 includes an axially extending raised ledge 230 at the end of external thread 208. The internal helical thread 198 of nut 36 defines a stop surface 234 due to the fact that thread 198 extends less than 360° in circumference. Nut 36 moves toward the proximal end of leadscrew 38 as leadscrew 38 moves within cartridge 40. Once nut 36 has axially moved entirely along thread 208 of leadscrew 38, nut 36 approaches axial ledge 230. Additional rotation of nut 36 results in nut 36 engaging ledge 230. This prevents the user from dialing up a higher dosage. Nut 36 may be rotated back in the opposite direction to reduce the dosage if desired. This rotational stop mechanism provides a very accurate indication to the user of the dosage remaining in the cartridge.

Once an injection is complete, nut 36 is prevented from rotating on leadscrew 38 until dial mechanism 34 is retracted relative to nut 36 to engage clutch teeth 144 of dial 34 with clutch teeth 192 of nut 36. If nut 36 were allowed to rotate while the clutch was disengaged, the nut would move along screw 38 and result in an inaccurate dosage. To prevent this rotation, housing parts 24 and 26 are provided with a plurality of locking elements in the form of ribs 197 (FIG. 4) which engage a plurality other locking elements in the form of prongs 196 (FIG. 10) provided on nut flange 194. Therefore, until dial mechanism 34 is retracted in the dose-setting position to engage the clutch, and dial mechanism 34 is rotated with enough force to disengage prongs 196 form ribs 197, ribs 197 will prevent nut 36 from rotating.

While this invention has been described as having an exemplary design, the present invention can be further modified within the spirit and scope of this disclosure. This application is therefore intended to cover any variations, uses, or adaptations of the invention using these general principles. Further, this application is intended to cover such departures from the present disclosure as come within known or customary practice in the art to which this invention pertains, and which fall within the limits of the appending claims.

What is claimed is:

1. A medication injection pen having a distal end and a proximal end, said pen comprising:

a housing defining an interior space;

a cartridge mounted within said housing interior space near said distal end and including a piston, an exit and an injectable medication between said piston and said exit;

a threaded drive stem mounted within said housing interior in axial alignment with said cartridge, said drive stem axially moveable through said cartridge for driving said piston and ejecting said medication from said cartridge;

a rotatable threaded nut threadingly disposed on said drive stem;

a dosage setting dial mechanism rotatably and axially shiftably mounted to said housing proximally of said cartridge, said dial mechanism having a dose-setting axial position and an end-of-injection axial position, said dial mechanism having a surface rotatably engaged with said nut when said dial mechanism is in said dose-setting axial position whereby rotation of said dial mechanism relative to said housing causes said nut to rotate relative to said drive stem to thereby set a dose, said dial mechanism having a second surface axially engaged with said nut during injection to thereby drive said drive stem distally, a distal limit of travel of said axially engaged dial mechanism and said nut relative to said housing defining said end-of-injection position for said dial mechanism and said nut;

said housing including at least one lock element engageable with a mating lock element on said nut when said nut is in said end-of-injection axial position, whereby rotation of said nut is inhibited in said end-of-injection position, rotation of said dial mechanism in said dose setting position transmitting sufficient torque to said nut to disengage said lock elements, wherein said at least one lock element comprises at least one rib disposed on an inner surface of said housing and said mating lock element comprises at least one prong which rotationally engages said at least one rib when said dial mechanism is in said end-of-injection axial position to thereby inhibit inadvertent rotation of said nut, rotation of said dial in said dose-setting position providing sufficient torque to force said at least one prong out of engagement with said at least one rib to thereby allow said nut to rotate about and axially translate along said drive stem.

2. A medication injection pen having a distal end and a proximal end, said pen comprising:

a housing defining an interior space;

a cartridge mounted within said housing interior near said distal end and including a piston, an exit, and an injectable medication between said piston and said exit;

a threaded drive stem mounted within said housing interior in axial alignment with said cartridge, said drive stem axially moveable through said cartridge for driving said piston and ejecting said medication from said cartridge;

a rotatable threaded nut threadingly disposed on said drive stem;

a dosage setting dial mechanism rotatably and axially shiftably mounted to said housing proximally of said cartridge, said dial mechanism having a dose-setting axial position and an end-of-injection axial position, said dial mechanism having a surface rotatably engaged with said nut when said dial mechanism is in said dose-setting axial position whereby rotation of said dial mechanism relative to said housing causes said nut to rotate relative to said drive stem to thereby set a dose, said dial mechanism having a second surface axially engaged with said nut during injection to thereby drive said drive stem distally, a distal limit of travel of said axially engaged dial mechanism and said nut relative to said housing defining said end-of-injection position for said dial mechanism and said nut;

said housing including at least one lock element engageable with a mating lock element on said nut when said nut is in said end-of-injection axial position, whereby rotation of said nut is inhibited in said end-of-injection position, rotation of said dial mechanism in said dose setting position transmitting sufficient torque to said nut to disengage said lock elements, wherein said housing further includes an end-of-injection bulkhead, said bulkhead disposed on said housing adjacent said end-of-injection position of said nut, said nut being provided with at least one engagement surface at a distal end thereof, said engagement surface axially engaging said bulkhead when an injection is complete to thereby prevent further telescopic insertion of said dial mechanism into said housing.

3. The pen of claim 2 wherein said bulkhead includes a plurality of tangs which engage a plurality of ratchet teeth provided along a longitudinal axis of said drive stem to allow movement of said drive stem with respect to said housing only in the direction of said distal end of said pen, a damping compound being provided between said tangs and said ratchet teeth to provide relatively slow, smooth, and quiet movement of said drive stem through said housing.

4. A medication injection pen having a distal end and a proximal end, said pen comprising:

a housing defining an interior space;

a cartridge mounted within said housing interior near said distal end and including a piston, an exit, and an injectable medication between said piston and said exit;

a threaded drive stem mounted within said housing interior in axial alignment with said cartridge, said drive stem axially moveable through said cartridge for driving said piston and ejecting said medication from said cartridge;

a rotatable threaded nut threadingly disposed on said drive stem;

a dosage setting dial mechanism rotatably and axially shiftably mounted to said housing proximally of said cartridge, said dial mechanism having a dose-setting axial position and an end-of-injection axial position, said dial mechanism having a surface rotatably engaged with said nut when said dial mechanism is in said dose-setting axial position whereby rotation of said dial mechanism relative to said housing causes said nut to rotate relative to said drive stem to thereby set a dose, said dial mechanism having a second surface axially engaged with said nut during injection to thereby drive said drive stem distally, a distal limit of travel of said axially engaged dial mechanism and said nut relative to said housing defining said end-of-injection position for said dial mechanism and said nut;

said housing including at least one lock element engageable with a mating lock element on said nut when said nut is in said end-of-injection axial position, whereby rotation of said nut is inhibited in said end-of-injection position, rotation of said dial mechanism in said dose setting position transmitting sufficient torque to said nut to disengage said lock elements, wherein said dial mechanism further includes a first outwardly projecting thread and a second outwardly projecting thread wherein said second thread includes two projections divided by a keyway, said housing further including a threaded surface defined by a helical land and a helical groove about an inner circumference thereof, a distal portion of said helical land including a first gap and a second gap, said second gap divided by a projecting key, axial proximal retraction of said dial mechanism relative to said housing being prevented in all rotational positions of said dial mechanism except where said first thread is aligned with said first gap and said second thread and keyway are aligned with said second gap and key.

5. A medication injection pen having a distal end and a proximal end, said pen comprising:

a housing defining an interior space;

a cartridge mounted within said housing interior space near said distal end and including a piston, an exit, and an injectable medication between said piston and said exit;

a threaded drive stem mounted within said housing interior in axial alignment with said cartridge, said drive stem axially moveable through said cartridge for driving said piston and ejecting said medication from said cartridge;

means for maintaining said drive stem in contact with said piston by preventing axial retraction of said drive stem away from said piston;

a rotatable threaded nut threadingly disposed on said drive stem;

a dosage setting dial mechanism rotatably mounted to said housing distally of said cartridge, said dial mechanism axially shiftable between a relatively proximal dose setting axial position and a relatively distal end-of-injection axial position, said dial mechanism having a first surface rotatably engaged with said nut by axially shifting said dial mechanism to said dose setting axial position whereby rotation of said dial mechanism relative to said housing causes said nut to rotate relative to said drive stem to thereby set a dose, said dial mechanism having a second surface axially engaged with said nut by axially shifting said dial mechanism from said dose setting position to said end-of-injection position to thereby drive said drive stem distally and discharge a selected dosage of said injectable medication, a distal limit of travel of said axially engaged dial mechanism and said nut relative to said housing defining said end-of-injection position, axially shifting said dial assembly to said end-of-injection position rotationally disengaging said dial mechanism first surface and said nut, wherein said nut includes at least one prong which rotationally engages at least one rib provided on an inner surface of said housing when said dial mechanism is in said end-of-injection position to thereby inhibit inadvertent rotation of said nut, rotation of said dial mechanism when said dial mechanism is in said dose-setting position providing sufficient torque to force said at least one prong out of engagement with said at least one rib to thereby allow said nut to rotate about and axially translate along said drive stem.

6. A medication injection pen having a distal end and a proximal end, said pen comprising:

a housing defining an interior space;

a cartridge mounted within said housing interior near said distal end and including a piston, an exit, and an injectable medication between said piston and said exit;

a threaded drive stem mounted within said housing interior in axial alignment with said cartridge, said drive stem axially moveable through said cartridge for driving said piston and ejecting said medication from said cartridge;

means for maintaining said drive stem in contact with said piston by preventing axial retraction of said drive stem away from said piston;

a rotatable threaded nut threadingly disposed on said drive stem;

a dosage setting dial mechanism rotatable mounted to said housing distally of said cartridge, said dial mechanism axially shiftable between a relatively proximal dose setting axial position and a relatively distal end-of-injection axial position, said dial mechanism having a first surface rotatably engaged with said nut by axially shifting said dial mechanism to said dose setting axial position whereby rotation of said dial mechanism relative to said housing causes said nut to rotate relative to said drive stem to thereby set a dose, said dial mechanism having a second surface axially engaged with said nut by axially shifting said dial mechanism from said dose setting position to said end-of-injection position to thereby drive said drive stem distally and discharge a selected dosage of said injectable medication, a distal limit of travel of said axially engaged dial mechanism and said nut relative to said housing defining said end-of-injection position, axially shifting said dial assembly to said end-of-injection position rotationally disengaging said dial mechanism first surface and said nut, wherein said housing further includes an end-of-injection bulkhead, said bulkhead disposed on said housing adjacent said end-of-injection position of said nut, said nut being provided with at least one engagement surface at a distal end thereof, said engagement surface axially engaging said bulkhead when an injection is complete to thereby prevent further telescopic insertion of said dial mechanism into said housing.

7. The pen of claim 6, wherein said bulkhead includes a plurality of tangs which engage a plurality of ratchet teeth provided along a longitudinal axis of said drive stem to allow movement of said drive stem with respect to said housing only in the direction of said distal end of said apparatus, a damping compound being provided between said ratchet teeth and said tangs to provide relatively slow, smooth, and quiet movement of said drive stem through said housing.

8. A medication injection pen having a distal end and a proximal end, said pen comprising:

a housing defining an interior space;

a cartridge mounted within said housing interior near said distal end and including a piston, an exit, and an injectable medication between said piston and said exit;

a threaded drive stem mounted within said housing interior in axial alignment with said cartridge, said drive stem axially moveable through said cartridge for driving said piston and ejecting said medication from said cartridge;

means for maintaining said drive stem in contact with said piston by preventing axial retraction of said drive stem away from said piston;

a rotatable threaded nut threadingly disposed on said drive stem;

a dosage setting dial mechanism rotatably mounted to said housing distally of said cartridge, said dial mechanism axially shiftable between a relatively proximal dose setting axial position and a relatively distal end-of-injection axial position, said dial mechanism having a first surface rotatably engaged with said nut by axially shifting said dial mechanism to said dose setting axial position whereby rotation of said dial mechanism relative to said housing causes said nut to rotate relative to said drive stem to thereby set a dose, said dial mechanism having a second surface axially engaged with said nut by axially shifting said dial mechanism from said dose setting position to said end-of-injection position to thereby drive said drive stem distally and discharge a selected dosage of said injectable medication, a distal limit of travel of said axially engaged dial mechanism and said nut relative to said housing defining said end-of-injeciton position, axially shifting said dial assembly to said end-of-injection position rotationally disengaging said dial mechanism first surface and said nut, wherein said dosage setting dial mechanism further includes a first outwardly projecting thread and a second outwardly projecting thread wherein said second thread includes two projections divided by a keyway, said housing further including a threaded surface defined by a helical land and a helical groove about an inner circumference thereof, a distal portion of said helical land including a first gap and a second gap, said second gap divided by a projecting key, axial proximal retraction of said dial mechanism relative to said housing being prevented in all rotational positions of said dial mechanism except where said first thread is aligned with said first gap and said second thread and keyway are aligned with said second gap and key.

9. A medication injection pen having a distal end and a proximal end, said pen comprising:

a generally hollow housing including a groove disposed in a plane oriented perpendicular to an axis of said housing and disposed on an inner surface of said housing and a helically threaded surface disposed on an inner portion of said housing;

a cartridge mounted within said housing near said distal end and including a piston, an exit, and an injectable medication between said piston and said exit;

a threaded drive stem mounted within said housing interior in axial alignment with said cartridge, said drive stem axially moveable through said cartridge for driving said piston and ejecting said medication from said cartridge;

a rotatable threaded nut threadingly disposed on said drive stem;

a dosage setting dial mechanism rotatably and axially shiftably mounted to said housing proximally of said cartridge, said dial mechanism having a dose setting axial position and an end-of-injection axial position, said dial mechanism having a surface rotatably engaged with said nut and a thread surface engaged with said helically threaded surface of said housing when said dial assembly is in said dose setting axial position, whereby rotation of said dial mechanism relative to said housing in said dose setting position causes said nut to rotate relative to said drive stem and said dial assembly to move axially proximally to thereby set a dose, said dial mechanism having a second surface axially engaged with said nut during injection to thereby drive said drive stem distally, a distal limit of travel of said axially engaged dial mechanism and said nut relative to said housing defining said end-of-injection position; and an end-of-injection click finger disposed on said dial mechanism, said click finger elastically deformable relative to said dial mechanism, said click finger snapping into said housing groove when said dial mechanism is in said end-of-injection position, wherein said nut includes at least one prong which rotationally engages at least one rib provided on an inner surface of said housing when said dial mechanism is in said end-of-injection position to thereby inhibit inadvertent rotation of said nut, rotation of said dial mechanism in said dose-setting position providing sufficient torque to force said at least one prong out of engagement with said at least one rib to thereby allow said nut to rotate about and axially translate along said drive stem.

10. A medication injection pen having a distal end and a proximal end, said pen comprising:

a generally hollow housing including a groove disposed in a plane oriented perpendicular to an axis of said housing and disposed on an inner surface of said housing and a helically threaded surface disposed on an inner portion of said housing;

a cartridge mounted within said housing near said distal end and including a piston, an exit, and an injectable medication between said piston and said exit;

a threaded drive stem mounted within said housing interior in axial alignment with said cartridge, said drive stem axially moveable through said cartridge for driving said piston and ejecting said medication from said cartridge;

a rotatable threaded nut threadingly disposed on said drive stem;

a dosage setting dial mechanism rotatably and axially shiftably mounted to said housing proximally of said cartridge, said dial mechanism having a dose setting axial position and an end-of-injection axial position, said dial mechanism having a surface rotatably engaged with said nut and a thread surface engaged with said helically threaded surface of said housing when said dial assembly is in said dose setting axial position, whereby rotation of said dial mechanism relative to said housing in said dose setting position causes said nut to rotate relative to said drive stem and said dial assembly to move axially proximally to thereby set a dose, said dial mechanism having a second surface axially engaged with said nut during injection to thereby drive said drive stem distally a distal limit of travel of said axially engaged dial mechanism and said nut relative to said housing defining said end-of-injection position; and an end-of-injection click finger disposed on said dial mechanism, said click finger elastically deformable relative to said dial mechanism, said click finger snapping into said housing groove when said dial mechanism is in said end-of-injection position, wherein said housing further includes an end-of-injection bulkhead, said bulkhead disposed on said housing adjacent said end-of-injection position of said nut, said nut being provided with at least one engagement surface at a distal end thereof, said engagement surface axially engaging said bulkhead when an injection is complete to thereby prevent further telescopic insertion of said dial mechanism into said housing.

11. The pen of claim 10, wherein said bulkhead includes a plurality of tangs which engage a plurality of ratchet teeth provided along a longitudinal axis of said drive stem to allow movement of said drive stem with respect to said housing only in the direction of said distal end of said apparatus, a damping compound being provided between said ratchet teeth and said housing tangs to provide relatively slow, smooth, and quiet movement of said drive stem through said housing.

12. A medication injection pen having a distal end and a proximal end, said pen comprising:

a generally hollow housing including a groove disposed in a plane oriented perpendicular to an axis of said housing and disposed on an inner surface of said housing and a helically threaded surface disposed on an inner portion of said housing;

a cartridge mounted within said housing near said distal end and including a piston, an exit, and an injectable medication between said piston and said exit;

a threaded drive stem mounted within said housing interior in axial alignment with said cartridge, said drive stem axially moveable through said cartridge for driving said piston and ejecting said medication from said cartridge;

a rotatable threaded nut threadingly disposed on said drive stem;

a dosage setting dial mechanism rotatably and axially shiftably mounted to said housing proximally of said cartridge, said dial mechanism having a dose setting axial position and an end-of-injection axial position, said dial mechanism having a surface rotatably engaged with said nut and a thread surface engaged with said helically threaded surface of said housing when said dial assembly is in said dose setting axial position, whereby rotation of said dial mechanism relative to said housing in said dose setting position causes said nut to rotate relative to said drive stem and said dial assembly to move axially proximally to thereby set a dose, said dial mechanism having a second surface axially engaged with said nut during injection to thereby drive said drive stem distally, a distal limit of travel of said axially engaged dial mechanism and said nut relative to said housing defining said end-of-injection position; and an end-of-injection click finger disposed on said dial mechanism, said click finger elastically deformable relative to said dial mechanism, said click finger snapping into said housing groove when said dial mechanism is in said end-of-injection position, wherein said dosage setting dial mechanism further includes a first outwardly projecting thread and a second outwardly projecting thread wherein said second thread includes two projections divided by a keyway, said housing further including a threaded surface defined by a helical land and a helical groove about an inner circumference thereof, a distal portion of said helical land including a first gap and a second gap, said second gap divided by a projecting key, said axial proximal retraction of said dial mechanism relative to said housing being prevented in all rotational positions of said dial mechanism except where said first thread is aligned with said first gap and said second thread and keyway are aligned with said second gap and key.

13. A medication injection pen having a distal end and a proximal end, said pen comprising:

a generally hollow housing including a helical groove disposed on an inner circumference thereof near said proximal end;

a cartridge mounted within said housing near said distal end and including a piston, an exit, and an injectable medication between said piston and said exit;

a threaded drive stem mounted within said housing in axial alignment with said cartridge, said drive stem axially moveable through said cartridge for driving said piston and ejecting said medication from said cartridge;

a rotatable threaded nut threading disposed on said drive stem;

a dosage setting dial mechanism rotatably, axially shiftably mounted to said housing proximally of said cartridge, said dial mechanism having a dose setting axial position and an end-of-injection axial position, said dial mechanism having a surface rotatably engaged with said nut when said dial mechanism is in said dose setting axial position whereby rotation of said dial mechanism relative to said housing causes said nut to rotate relative to said drive stem to thereby set a dose, said dial mechanism having a second surface axially engaged with said nut during injection to thereby drive said drive stem distally, a distal limit of travel of said axially engaged dial mechanism and said nut relative to said housing defining said end-of-injection position, said dial mechanism including first and second threads on an outer circumference thereof, said threads being threadingly engageable with said housing helical groove and resiliently deformable radially inwardly and outwardly relative to said dial mechanism; and a button telescopically received in a proximal end of said dial mechanism, said button having a distal end having a first circumferential step and a second circumferential step, said first step having a enlarged diameter, said second step having a larger diameter than said first step, said first step engaging and biasing said deformable threads outward into engagement with said helical groove and thereby preventing said dial mechanism from non-rotationally axially advancing relative to said housing with said first step engaged with said deformable threads, said second step engaging said dial mechanism to prevent said button from being fully retracted out of said pen, said button adapted to be telescopically axially advanced within said dial mechanism to thereby move said first step out of engagement with said deformable threads to thereby allow said threads to deform inward and out of engagement with said helical groove, said dial mechanism thereby being non-rotationally axially advanceable relative to said housing with said first step disengaged from said deformable threads.

14. The pen of claim 13, wherein said button further includes a third enlarged diameter portion between said first step and said proximal end, said third enlarged diameter portion engaging an elastically deformable and inwardly ramped surface on said dial mechanism, said ramped surface deforming outward when said button is depressed to allow for an injection, said ramped surface biasing said button toward said proximal end of said pen when said button is not depressed.

15. The pen of claim 13, wherein said second thread is divided by a keyway, and said housing helical groove includes a first gap and a second gap, said second gap divided by a projecting key, said axial proximal retraction of said dial mechanism relative to said housing being prevented in all rotational positions of said dial mechanism except where said first thread is aligned with said first gap and said second thread and keyway are aligned with said second gap and key.

16. The pen of claim 13 wherein said nut includes at least one prong which rotationally engages at least one rib provided on an inner surface of said housing when said pen is in said non-dose setting position to thereby inhibit inadvertent rotation of said nut, rotation of said dial mechanism in said dose-setting position providing sufficient torque to force said at least one prong out of engagement with said at least one rib to thereby allow said nut to rotate about and axially translate along said drive stem.

17. The pen of claim 13, wherein said nut includes a plurality of clutch teeth disposed on an outer surface thereof, said nut being telescopingly received within said dial mechanism when said dial mechanism is in said dose-setting position, said clutch teeth rotationally engaging a plurality of receiving splines provided on an inner surface of said dial mechanism when said dial mechanism is in said dose-setting position, said dial mechanism being telescopingly inserted into said housing when being moved to said end-of-injection position and thereby causing said receiving splines to become disengaged from said clutch teeth when said dial mechanism is in said end-of-injection position.

18. The pen of claim 13, wherein said housing further includes a centering ring around an inner circumference thereof and about a distal end of said dial mechanism to maintain proper alignment of said dial mechanism within said housing.

19. The pen of claim 13, wherein said drive stem further includes a helical thread about its exterior and a stop disposed near a proximal end of said stem, said nut having a surface positioned to rotationally engage said stop when said nut has reached a predetermined axial position on said drive stem and thereby prevent further proximal movement of said drive stem.

20. The pen of claim 13, wherein said housing further includes an end-of-injection bulkhead, said bulkhead disposed on said housing adjacent said end-of-injection position of said nut, said nut being provided with at least one engagement surface at a distal end thereof, said engagement surface axially engaging said bulkhead when an injection is complete to thereby prevent further telescopic insertion of said dial mechanism into said housing.

21. The pen of claim 20, wherein said bulkhead includes a plurality of tangs which engage a plurality of ratchet teeth provided along a longitudinal axis of said drive stem to allow movement of said drive stem with respect to said housing only in the direction of said distal end of said apparatus, a damping compound being provided between said ratchet teeth and said tangs to provide relatively slow, smooth, and quiet movement of said drive stem through said housing.

22. The pen of claim 13 wherein said housing is comprised of two semicylindrical plastic portions having longitudinal edges, said longitudinal edges being aligned and ultrasonically welded together to form a cylinder.

23. The pen of claim 13 wherein said housing further includes a circular groove about an inner circumference thereof, and said dial mechanism includes an end-of-injection click finger, said click finger elastically deformable relative to said dosage setting dial, said click finger snapping into said housing circular groove when an injection is complete to provide the user with an audible indication thereof.

* * * * *